United States Patent [19]

Halpern

[11] Patent Number: 4,532,661
[45] Date of Patent: Aug. 6, 1985

[54] FEMORAL HEAD REMODELING AND PROSTHETIC MEANS THEREFOR

[76] Inventor: Alan A. Halpern, 2830 Duke St., Kalamazoo, Mich. 49008

[21] Appl. No.: 376,111

[22] Filed: May 7, 1982

[51] Int. Cl.³ ............................ A61F 1/04; A61F 5/04
[52] U.S. Cl. .................................. 623/23; 128/92 C; 128/92 CA; 623/18
[58] Field of Search ....................... 3/1.9, 1.91, 1.912, 3/1.913; 128/92 C, 92 CA, 92 G, 92 BC

[56] References Cited

U.S. PATENT DOCUMENTS

| | | | |
|---|---|---|---|
| 2,781,758 | 2/1957 | Chevalier | 3/1.913 |
| 3,918,441 | 11/1975 | Getscher | 128/92 BC |
| 4,068,324 | 1/1978 | Townley et al. | 3/1.913 |
| 4,199,824 | 4/1980 | Niederer | 3/1.913 |
| 4,312,079 | 1/1982 | Dorre et al. | 3/1.913 |

FOREIGN PATENT DOCUMENTS 1316809 8/1975 United Kingdom .................. 3/1.9

Primary Examiner—R. J. Apley
Assistant Examiner—David J. Isabella
Attorney, Agent, or Firm—Gordon W. Hueschen

[57] ABSTRACT

A femoral hip joint replacement comprises a hollow metal cap, approximating the normal femoral head size, secured to a tri-flanged insert adapted to be located within the femoral shaft and between remaining upstanding portions of the remodeled femoral head. The cap is secured to or integral with the upper surface of the insert head and rests upon the superior portion of the remodeled femoral head which has been cut downwardly at an angle of approximately 23 degrees in relation to a plane normal to the vertical axis of the femoral shaft. The sides and end of the femoral head are also resected to provide flat faces, and the upper surface of the remodeled femoral head also preferably angles upwardly front-to-back at an angle of approximately seven degrees, these angles imparting superior load-bearing characteristics to the structure in operation. The insert neck is seated on the inner surface of the cortex of the medial portion of the remodeled femur at the calcar or inferior femoral neck, and the metal shell has inner mating faces corresponding to the faces of the remodeled femoral head to facilitate close engagement therewith and securement thereto. The inner portion of the metal shell and the insert are preferably porous-coated to allow direct ingrowth of bone. Following placement of the prosthetic insert within the femoral shaft, the surgeon has the option of further securing or not securing the insert with cement.

44 Claims, 22 Drawing Figures

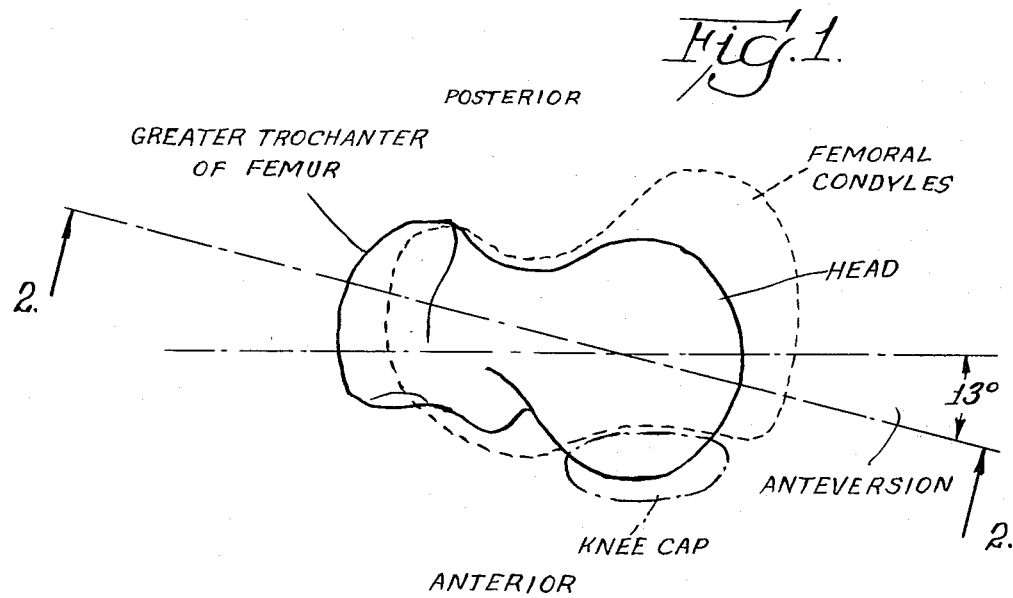
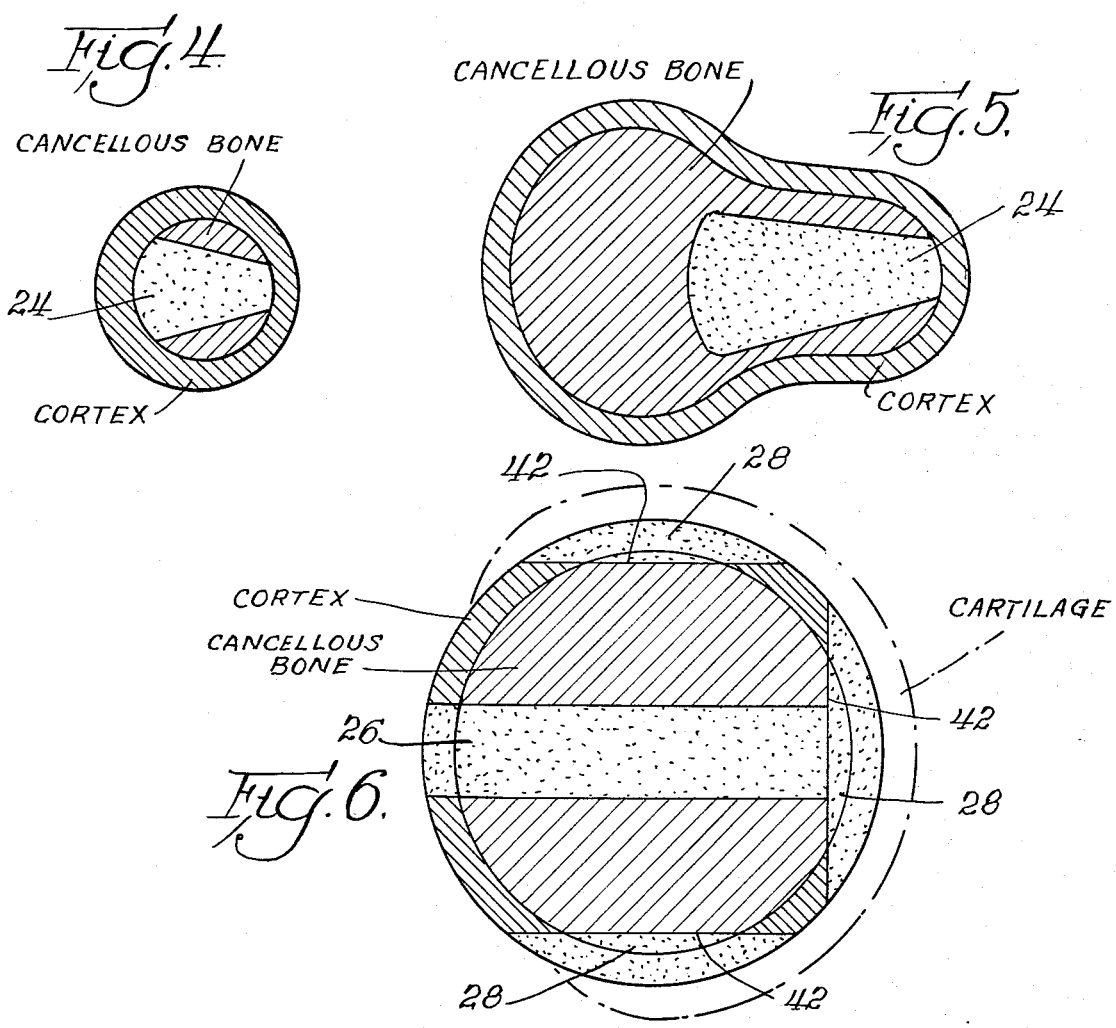

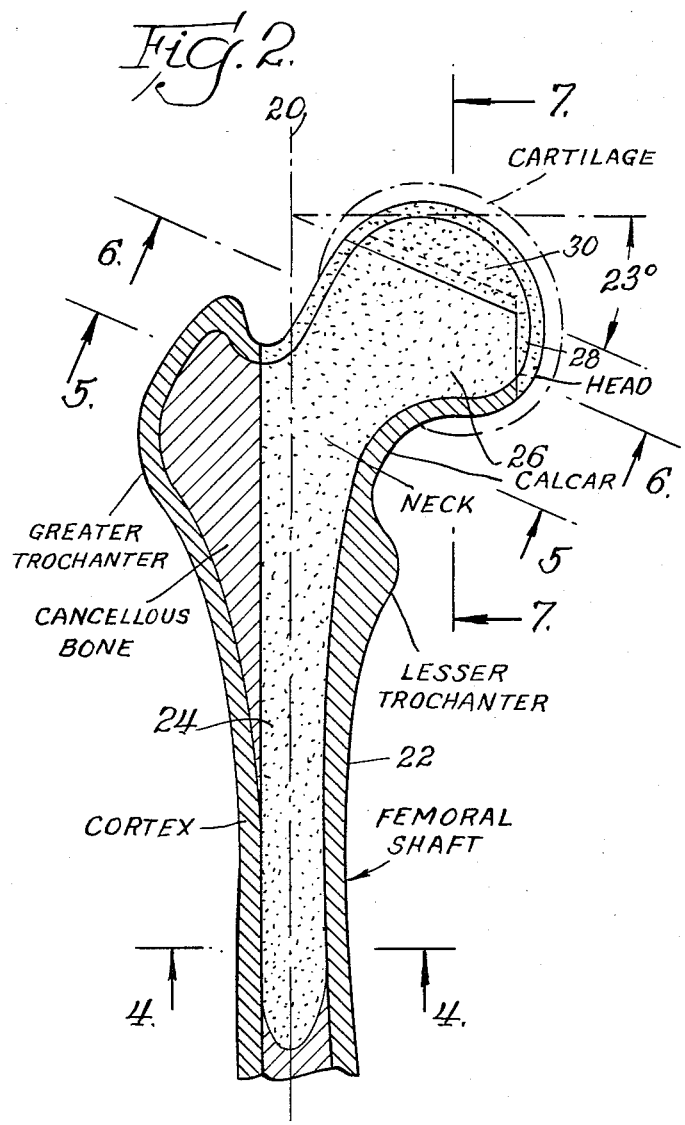
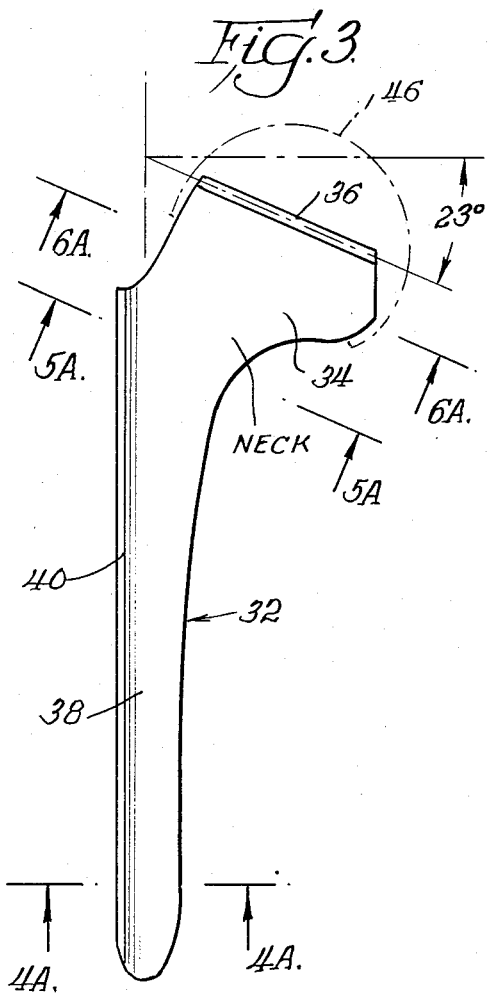
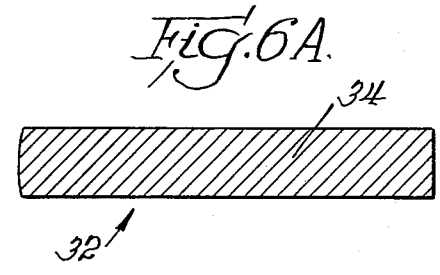
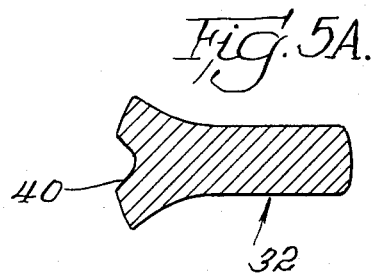
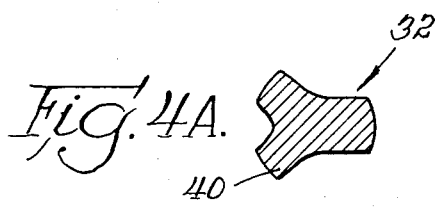

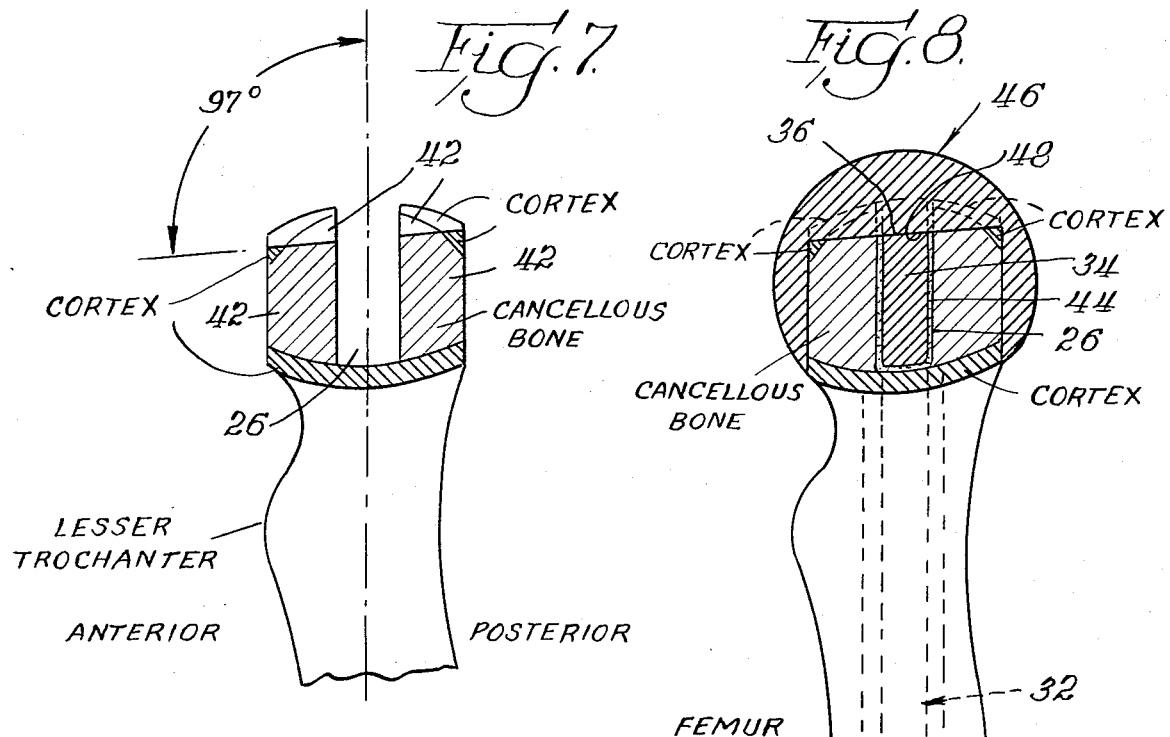
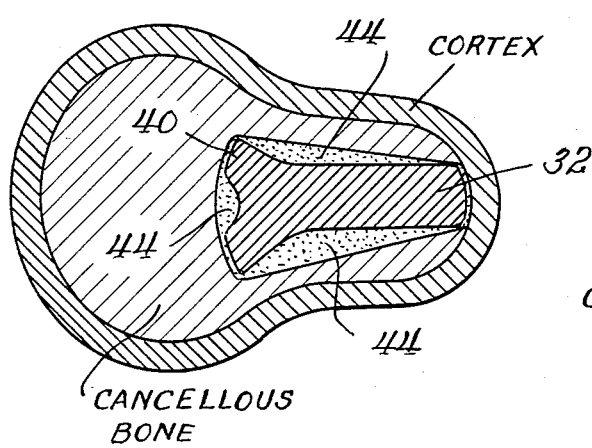
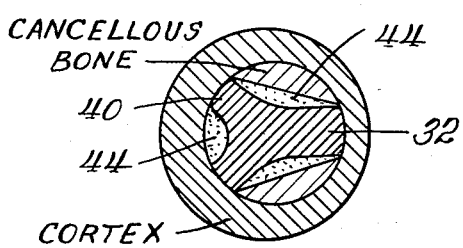

CORTEX
CANCELLOUS BONE

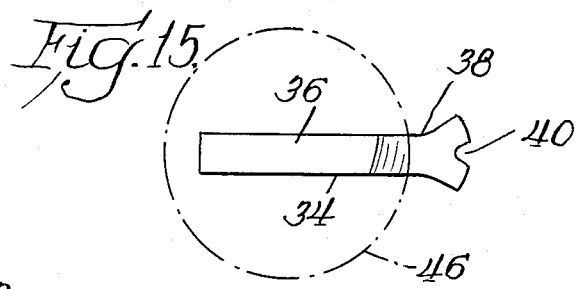
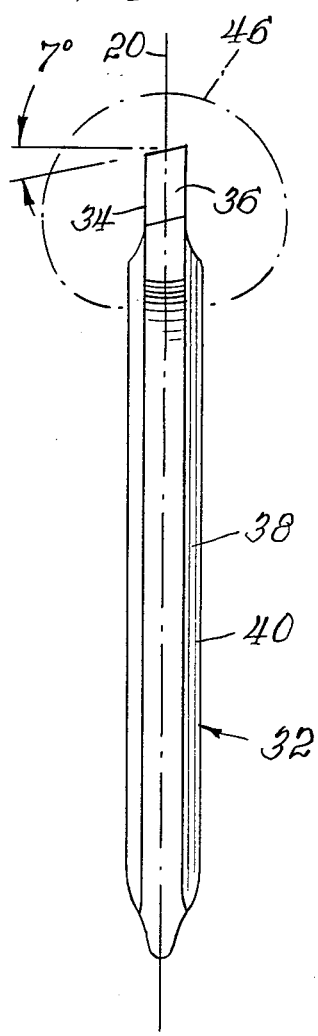
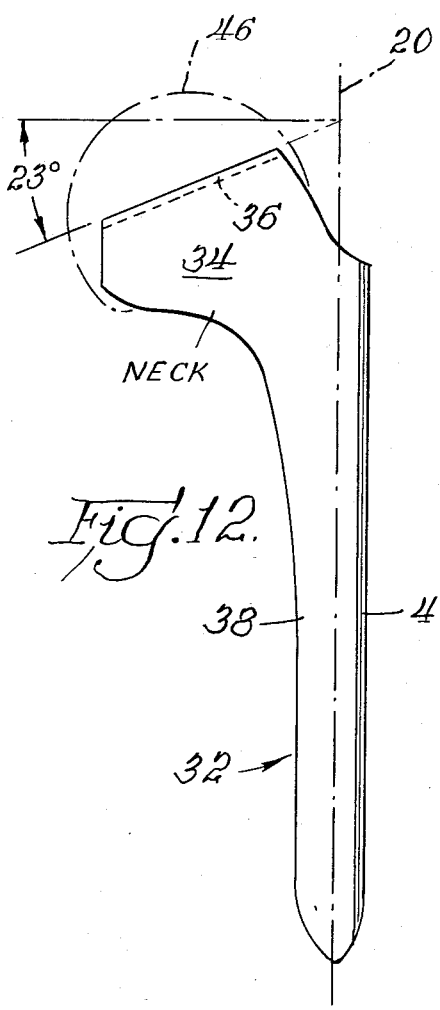
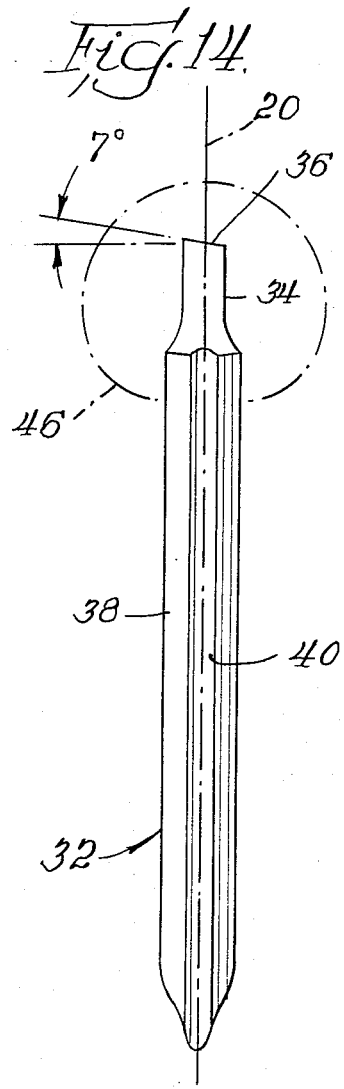
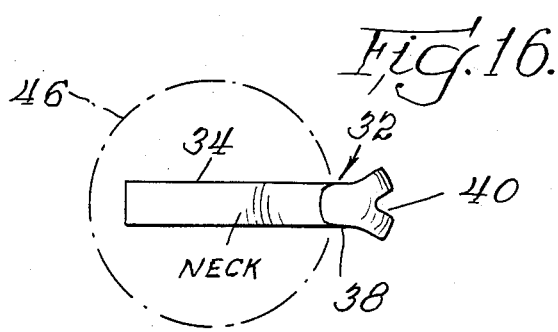

FEMORAL HEAD REMODELING AND PROSTHETIC MEANS THEREFOR

BACKGROUND OF THE INVENTION

1. Field of Invention

This invention relates to a novel method for remodeling of the femoral head and to prosthetic means, including an intramedullary insert and integral shell or cap, for use as a part of the said femoral head remodeling procedure.

The ultimate product of the present invention may be employed with an intact acetabula, namely, the cup-shaped socket in the hip bone, or in combination with prosthetic acetabular sockets or cups, which are widely available from orthopaedic supply organizations today and which are well known in the art. A representative prosthetic acetabular socket is disclosed in U.S. Pat. No. 3,722,002. Representative orthopaedic supply houses specializing in prosthetic acetabular sockets include DePuy, Howmedica, and Zimmer, the latter of which also specializes in Amstutz-developed femoral head prosthetic devices and total hip joint replacement prosthetic components.

As is well known in the art, the hip joint comprises the acetabula or an acetabular prosthesis, which is a cup-shaped socket in the hip bone, providing a generally hemispheric surface, within which the femoral head, having a corresponding generally hemispheric surface contour, rotates by means of a thin layer of cartilage under normal conditions and on a thin layer of plastic or the like under conditions of reconstruction and prosthesis after the normal cartilage has become eroded or the hip joint has become otherwise inoperative due to aging, inury, or other abnormal conditions arising from any of a multitude of etiologies.

The ultimate product of the present invention, which is a femur having a remodeled femoral head including prosthetic means comprising the intramedullary insert and its integral cap, is intended for use in cooperation with a normal or prosthetic acetabular socket, but the provision of such acetabular socket does not constitute a part of the present invention.

2. Prior Art

The prior art is replete with procedure and prosthetic means for remodeling of the femoral head. Most of the intramedullary inserts are curved and have a ball at the upper end to replace the femoral head itself. Further, most procedures and prosthetic means for implementing the same involve resection of the femoral head at a point just above the lesser trochanter at approximately the calcar or inferior neck of the femur, the resection being made on an angle approximately 45 degrees from the horizontal and commencing just above the greater trochanter and ending at the calcar or inferior neck of the femur just above the lesser trochanter. However, in many instances, such resection results in the elimination of considerable healthy cancellous bone and cortex of the femoral head and otherwise lying above the lesser trochanter and calcar, with the result that maximum utilization of existing and utilizable portions of the femur lying above the lesser trochanter and calcar is not effected. Further, according to most prior art procedures and prosthetic devices therefor, the intramedullary insert is usually inserted into the intramedullary canal or femoral shaft at an angle, and only a relatively small portion thereof is in line with the vertical axis of the intramedullary canal or femoral shaft, providing less than maximum support for the femoral insert within the femoral shaft and remodeled femur. Additionally, such femoral inserts have been less than adequately stabilized in their desired position within the femoral shaft, resulting in a twisting, turning, and displacement effect after the remodeled femur has been placed into use. Further, the existing procedures and femoral inserts have failed to provide an osteotomy and femoral insert in which the opposing surface angles in the remodeled femoral head are essentially perpendicular to the lines of force imparted by the hip during normal gait, thereby to decrease the shear force applied to the remodeled femoral head and resulting in inherent stability thereof in actual use of the remodeled femur.

Representative U.S. Patents in this field include No. 3,314,420, which shows a porous ceramic body formed of one material which can be used in the creation of a femoral insert; No. 3,510,883, which shows a typical femoral insert including femoral head, just as does the earlier-cited patent Nos.; Nos. 3,694,820; 3,744,061; 3,781,917; 3,808,606, which shows a type of porous coating which can be employed on a femoral insert; Nos. 3,815,590; 3,843,975; 3,855,638, which again shows a porous coating which may be employed on the external surface of a femoral insert; No. 3,893,196, which shows another material of construction which can be used for a femoral insert; Nos. 3,922,726; 3,925,824; 3,938,198, which presents a detailed review of the art; No. 3,965,490, which relates to commercially-available prosthetic means and discloses certain alloys which can be used as material of construction for femoral inserts; No. 4,012,796, which shows a femoral insert having an "interpositioning collar"; 4,021,865, which employs a flange and serrations to impede separation of the insert from the femoral shaft; No. 4,035,848, which discloses a specific hip capitulum cap; No. 4,064,567, which discloses a woven basket cover for the prosthetic device to improve the gripping surface thereof; No. 4,068,324, which discloses a combination of an artificial femoral head and acetabular socket; No. 4,123,806, which provides an excellent review of the prior art and medical terms involved; No. 4,141,088, which discloses a representative femoral insert; No. 4,156,943, which discloses another porous material which may be employed in the production of a femoral insert; and No. 4,206,516, which discloses another porous coating, in this case a metal porous coating, which may employed on the outer surface of a femoral implant to support ingrowth of bone tissue for fixation of the device within the femoral shaft.

OBJECTS OF THE INVENTION

It is an object of the present invention to provide a novel method for the remodeling of a femoral head in need thereof. Another object is the provision of such a method which involves the employment of novel prosthetic means. A further object is the provision of such a method in which the amount of bone resected from the femoral head is minimized, and much of the cancellous bone and cortex of the femoral head lying above the lesser trochanter and calcar retained. An additional object is the provision of such a method wherein the osteotomy performed on the superior neck and head provides a surface which is perpendicular to the lines of force of the hip during normal gait, and thus decreases the shear force applied to the said surface, and therefore provides for enhanced stability of the remodeled femoral head and various components thereof. Still a further object of the invention is the provision of such a method wherein the superior surface of the osteotomy lies at an acute angle with respect to a plane normal to the vertical axis of the femoral shaft or intramedullary canal, said surface preferably also rising at an acute angle from the anterior to the posterior of said femoral head. A still further object is the provision of such a method which involves providing an opening in the superior neck and excavating a portion of the intramedullary canal, then cutting away an internal portion from said opening into said femoral head, inserting said femoral insert, cutting the superior surface of the remaining upstanding portions of the femoral head so as to provide a surface perpendicular to the lines of force of the hip during normal gait, squaring off the sides of the femoral head and the end of the head opposite the greater trochanter to provide substantially vertical planes, securing said insert within the femoral shaft or intramedullary canal, including the use of medical cement or the like if desired, and securing a femoral head cap or shell to the remaining upstanding portions of the femoral head, said cap having an inner contour corresponding to the outer contour then provided by the osteotomy and an outer surface which is generally hemispherical and essentially corresponding to the surface of the original femoral head and, if desired, closing the opening provided at the top of the femoral shaft. Other objects of the invention include providing such superior surface of the osteotomy at a downward angle of approximately 23 degrees with respect to a plane normal to the vertical axis of said femoral shaft, providing said surface with an angle of approximately 7 degrees from front to back, and securing the femoral insert so that the bottom of the right-angled protuberance or head thereof is seated in contact with the remaining calcar and medial femoral cortex, thereby to minimize the likelihood of settling of the insert. Still an additional object of the invention is the provision of such a femoral insert, including a femoral head cap, wherein the stem of said insert designed to be secured within the intramedullary canal is tri-flanged at least along a portion of its longitudinal axis for better and more positive securement within the femoral shaft, wherein the upper end or head of the femoral insert is of elongated rectangular cross-section, and wherein the femoral insert and its femoral cap is so designed to provide substantial interlocking relationship between the opposed mating surfaces of the femoral insert and the surfaces remaining in the femoral head after the osteotomy so as to ensure positive locking engagement between said cap or shell and the remainder of said remodeled femoral head. Other objects will be obvious to one skill in the art, and still other objects will become apparent hereinafter.

SUMMARY OF THE INVENTION

The invention may be summarized essentially as follows:

A femoral insert, adapted to be secured in a femoral shaft as a part of a femoral hip joint replacement, comprising an elongated shaft with a longitudinal axis generally corresponding to the vertical axis of a femoral shaft, said insert comprising a stem portion, a neck portion, and a head portion constituting an offset to the longitudinal axis of said shaft, said head portion having a cross-section of the nature of an elongated rectangle, to permit seating thereof between two vertically-upstanding portions of a remodeled femoral head having an opening therebetween generally corresponding to the cross-section of said head portion, said head portion being secured to or integral with a femoral cap; such insert wherein said shaft is flanged along at least a portion thereof so as to permit three-point contact of said shaft with the interior of said femoral shaft when said flanged portion is in place therein; such insert wherein said neck portion of said insert is adapted to be seated on cortex at the calcar of said femur and is contoured to correspond approximately to the interior contour of the calcar of said femur; such insert wherein the head portion of said insert is a righthanded offset to said shaft and has an essentially downwardly vertical face at the end thereof; such insert wherein the front, back, and end surfaces of said head of said insert are substantially flat vertical planes; such insert wherein said shaft of said insert comprises a Y-shaped cross-section along at least a portion thereof; such insert wherein said Y-shaped cross-section is present at said stem portion and said neck portion of said insert; such insert having an irregular or porous surface; also, such insert wherein said cap comprises an outer hemispherical shell substantially corresponding to the normal femoral head and of a size approximately that of the femoral head being replaced, and has an inner surface and contours adapted to correspond to the superior surface of a remodeled femoral head which is essentially squared off at its front, back, and end, and which has a downwardly-slanting superior surface resected therein, which downwardly-slanting surface is at an acute angle, preferably between about twenty and thirty degrees and especially about 23 degrees, with respect to a line normal to the vertical axis of the femoral shaft to which said remodeled femoral head is attached, the interior of said cap having surfaces therein which corresponds to the outer surfaces of said remodeled femoral head for positive mating relation of said surfaces when said cap is in place over said remodeled femoral head; wherein said cap has an irregular or porous interior surface; wherein said downwardly-slanting superior surface is also angled upwardly from front to back at an acute angle, preferably less than about ten degrees and especially about seven degrees; also a method of providing a femoral hip joint replacement comprising the steps of providing an opening at the superior neck of the femur, providing an elongated excavation within the femoral shaft generally corresponding to the shaft of a femoral insert to be inserted therein and essentially in line with the vertical axis of said femoral shaft, providing an elongated aperture in said femoral head so as to leave two upstanding vertical sections of said femoral shaft with a generally elongated rectangular aperture therebetween, imparting a superior surface to the remaining vertically-upstanding portions of said femoral head which slants downwardly at an acute angle with respect to a line normal to the vertical axis of said femoral shaft to present a plane which is adapted to be essentially perpendicular to the lines of force imparted to the femoral portion of a hip joint during normal human gait, providing a femoral insert within the excavated portion of said femoral shaft, said insert comprising an elongated shaft having a longitudinal axis generally corresponding to the vertical axis of said femoral shaft and having a stem portion, a neck portion, and an offset head portion, said head portion being of generally elongated rectangular cross-section and adapted to lie within the generally elongated rectangular aperture provided in said femoral head between said remaining vertically-upstanding portions of said remodeled femoral head, said head portion of said insert having a femoral cap secured thereto to integral therewith, and securing said shaft within said femoral shaft, said head portion in place between said remaining vertically-upstanding portions of said remodeled femoral head, and said femoral cap in place over said remodeled femoral head; such method wherein said superior surface of said remaining vertically-upstanding portions of said femoral head angle downwardly between about twenty and thirty degrees, preferably about 23 degrees, with respect to said normal line; such method wherein the said superior surface is also angled upwardly from the front to the back of said superior surface at a slight acute angle, preferably less than about ten degrees and especially about seven degrees; such method wherein said shaft of said insert is flanged along at least a portion thereof so as to provide three-point contact of said flanged portion of said shaft with said femoral shaft; such method wherein said shaft of said insert comprises a Y-shaped cross-section along at least a portion thereof; such method wherein said Y-shaped cross-section is present at said stem portion and said neck portion of said insert; such method wherein the shaft of said insert is secured within the femoral shaft without the employment of medically-acceptable cement; such method wherein the shaft of said femoral insert is secured within the femoral shaft with the aid of medically-acceptable cement; such method wherein the head portion of said insert is secured within said aperture with the aid of medically-acceptable cement; such method wherein the head of said insert comprises a right-handed offset to the shaft of said insert; such method wherein the neck of said insert is seated on the inner surface of the cortex of the remodeled femur at the calcar; such method wherein the femoral insert is contoured at its neck to correspond substantially with the contour of the inner surface of the cortex of the calcar and is seated against the inner surface of the cortex of the remodeled femur at the calcar; such method wherein the end of said femoral head is squared off at the end of said slanting superior surface thereof; such method wherein the front, back, and end of said femoral head are squared off; such method wherein the squaring off of said femoral head presents essentially flat and vertical faces on the front, back, and end of said remodeled femoral head for close and mating engagement with corresponding surfaces provided interior of said femoral cap which is secured in place over said femoral head; such method wherein said femoral cap is substantially hemispherical and has a size and contour essentially corresponding to the outer surface and contour of the femoral head being replaced; such method wherein internal faces and contours of said cap correspond to surfaces provided in said remodeled femoral head and lie in close juxtaposition and in mating engagement with the corresponding surfaces of said remodeled femoral head when said cap is in place thereover; such method wherein said cap is secured over the end of said remodeled femoral head with the aid of medically-acceptable cement; such method wherein said insert has an irregular or porous surface; such method wherein said insert has an irregular or porous surface and said cap has an irregular or porous interior surface; such method wherein, after completion of the remodeling of the femoral head, the opening originally provided in the superior neck of the femur is closed; and finally, a femoral insert, adapted to be secured in a femoral shaft as a part of a femoral hip joint replacement, comprising an elongated shaft with a longitudinal axis generally corresponding to the vertical axis of a femoral shaft, said insert comprising a stem portion, a neck portion, and a head portion constituting an offset to the longitudinal axis of said shaft, said head portion having a cross-section of the nature of an elongated rectangle, to permit seating thereof between two vertically-upstanding portions of a remodeled femoral head having an opening therebetween generally corresponding to the cross-section of said head portion, especially such insert wherein said shaft is flanged along at least a portion thereof so as to permit three-point contact of said shaft with the interior of said femoral shaft when said flanged portion is in place therein; such insert wherein said head portion comprises a superior surface which angles downwardly between about twenty and about thirty degrees with respect to a line drawn normal to the longitudinal axis of said shaft, preferably wherein said downward angle is about 23 degrees with respect to said normal line, especially wherein said superior surface is also angled upwardly from the front to the back of said superior surface at a slight acute angle, particularly wherein the said superior surface is angled from the front to the back of said superior surface at an angle less than about ten degrees, and preferably wherein said angle is about seven degrees.

BRIEF DESCRIPTION OF THE DRAWINGS

In the drawings:

FIG. 1 is a diagrammatic top view of the greater trochanter, femoral head and superior neck, femoral condyles, and knee cap, the femoral shaft running into the drawing behind the femoral head;

FIG. 2 is a cross-sectional view taken along line 2—2 of FIG. 1 (which indicates a verticle plane bisecting the femoral neck and head in FIG. 1) at the upper portion of the femur, showing the areas to be excavated from the femoral shaft and the areas to be resected from the femoral head;

FIG. 3 is a side view of the lower portion of a femoral insert according to the invention, the attached femoral cap being shown in shadow lines;

FIG. 4 is a cross-section of the femoral shaft taken along line 4—4 of FIG. 2 after excavation as by reaming;

FIG. 4A is a cross-section of the insert of FIG. 3 taken along line 4A—4A thereof;

FIG. 4B is a cross-section taken along line 4—4 of FIG. 2 with the insert of FIG. 3 in place;

FIG. 5 is a cross-section of the femoral shaft taken along line 5—5 of FIG. 2 after reaming;

FIG. 5A is a cross-section of the insert of FIG. 3 taken along line 5A—5A thereof;

FIG. 5B is a cross-section taken along line 5—5 of FIG. 2 with the insert of FIG. 3 in place;

FIG. 6 is a cross-section of the femoral head taken along line 6—6 of FIG. 2 after reaming and cutting, indicating side and end flats to be cut;

FIG. 6A is a cross-section of the insert of FIG. 3 taken along line 6A—6A thereof;

FIG. 7 is a medial view along line 7—7 of FIG. 2 showing the remodeled femoral head, prior to insertion of the insert, but leaving out the greater trochanter in the background;

FIG. 8 is the same view as FIG. 7 taken on line 8—8 of FIG. 9 with the insert including the femoral cap in place;

FIGS. 4, 4A, 4B, 5, 5A, 5B, 6, 6A and 6B being enlarged.

FIG. 12 is the same as FIG. 3, viewed from the opposite side.

FIG. 13 is a left-side view of FIG. 12.

FIG. 14 is a right-side view of FIG. 12.

FIG. 15 is a top view of FIG. 12, and

FIG. 16 is a bottom view of the insert of FIG. 12, which insert is at all times the same insert as shown in FIG. 3, FIG. 7, and all other preceding FIGS. of the drawings.

DETAILED DESCRIPTION OF THE INVENTION

In accord with usual methodology for total or partial hip joint replacement, following dislocation of the hip joint, the minimum amount of bone is removed from the surface of the head of the femur to expose healthy, firm bone surfaces, whereafter the prosthetic femoral insert is placed into position and secured in such position to provide a replacement hip joint surface, ordinarily of metal, having the configuration of a ball (i.e., the femoral head) of substantially the same size and in substantially the same location as the original ball, whereafter the capped ball and the acetabulum or acetabulum socket member are relocated in rotatable engagement with one another.

From FIG. 1 is seen the top of the femoral head in its relation with other relevant members, angled slightly forward, the extent of the anteversion indicated at adulthood being approximately thirteen degrees from the vertical body plane. Line 2—2 in FIG. 1 bisects the femoral neck and head for purposes of providing the cross-sectional view of FIG. 2.

Figure 11:
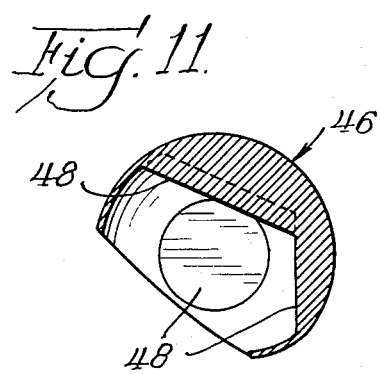
FIG. 11 is a cross-sectional view of the isolated femoral cap of FIG. 10, taken along line 11—11 of FIG. 10.

FIG. 2 shows the areas to be excavated from the femoral shaft and areas to be resected from the femoral head, beginning at the superior neck thereof. The cartilage is shown in shadow lines but, in the case of a normal hip replacement situation, is usually damaged or at least partially non-existent. Line 20 here indicates the vertical center of the femoral shaft, and the indicated line of resection of the femoral head beginning at the superior neck angles approximately 23 degrees downwardly from a line normal to the said vertical axis 20. Toward the end of the femoral head, at the end of the angled line of resection, the line of resection drops substantially vertically, to provide a flat face for mating engagement with the flat face 48 of cap 46, ultimately intended to be secured in place over the remodeled femoral head. The isolated cap is shown in greater detail in FIGS. 9, 10, and 11, but is ordinarily secured (as by welding) to or integral with head portion 34 of insert 32.

Figure 6B:
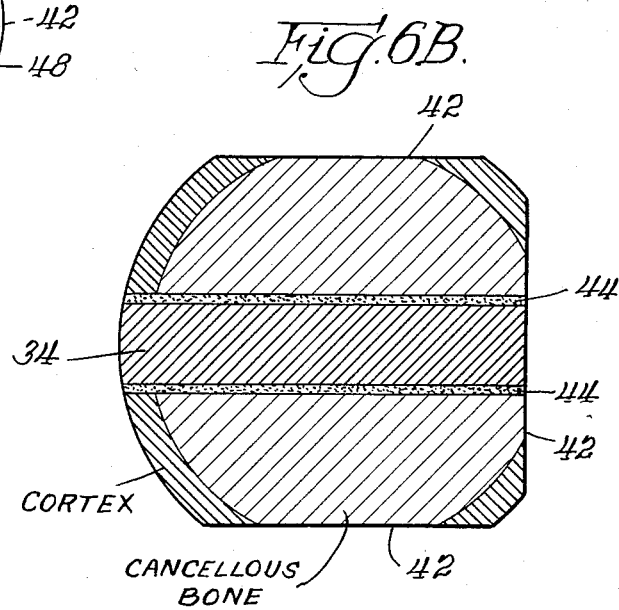
FIG. 6B is a cross-section taken along line 6—6 of FIG. 2 with the insert of FIG. 3 in place, and after cutting side and end flats.

Also shown in FIG. 2 is the femoral shaft, which contains therein the intramedullary canal comprising cancellous bone within the outer cortex. At 24 is indicated the opening within the femoral shaft or intramedullary canal which is intended to be excavated, as by rasping or reaming, and at 26 is indicated an opening intended to be cut out or otherwise excavated in the femoral head and neck. The femoral head is squared off at 28 to provide substantially flat and vertical surfaces 42 at the front, back, and end of the femoral head during the process of remodeling, as shown in FIGS. 6 and 6B. At 30 in FIG. 2 is indicated the cut-off at the top of the femoral neck and head which not only angles approximately 23 degrees downwardly from a line normal to (that is, downwardly from a right-angle line drawn perpendicular to the vertical axis) vertical axis 20, but also is preferably angled from front to back across the top of the remaining femoral head at an angle of approximately 7 degrees (that is, downwardly seven degrees from a right-angle line drawn perpendicular to the vertical axis 20), as further clearly shown in FIG. 7.

FIG. 3 shows the lower portion of a tri-flanged insert, adapted to be located within the excavated femoral shaft, and also between the remaining upstanding portions of the remodeled femoral head. The insert 32 has a shaft with a longitudinal axis corresponding generally to vertical axis 20 of the femoral shaft or intramedullar canal, said shaft having a right-handed offset at its top to provide a head portion 34 connected to stem portion 38 by a neck, the entire contour of the insert as shown in FIG. 3 being adapted to correspond essentially with the area desired to be excavated from the femur and to correspond with the aperture remaining between upstanding portions of the femoral head intended to remain after resection thereof. The insert neck is designed and adapted to seat upon the remaining cortex at the femur inferior neck or calcar. The insert comprises a Y-shaped section 40, which imparts a tri-flanged cross-section to insert 32 at 4A—4A and 5A—5A, as shown in FIGS. 4A and 5A, these cross-sections being taken at the stem portion and approximately at the neck portion of insert 32. At head portion 34 of insert 32, the cross-section is no longer Y-shaped, but is generally elongated rectangular with possibly somewhat rounded corners as shown in FIG. 6A. The femoral cap 46 (see FIGS. 8, 9 and 11), which is ordinarily integral with head portion 34 of insert 32, or secured thereto by welding, brazing, or the like, is shown in shadow lines in FIG. 3.

The cross-section of the femoral shaft at 4—4, after excavation is as shown in FIG. 4, the aperture 24 being provided by reaming or rasping out, preferably with a rasp of a cross-section corresponding generally to the cross-section of area 24 in FIG. 4. The cross-section of the femoral shaft at 5—5, at approximately the calcar or inferior neck thereof, taken through the upper portion at the greater trochanter, is approximately as shown in FIG. 5, wherein once again the cross-section of the aperture 24 preferably corresponds in general to the cross-section of the rasp employed for providing the same (or vice versa). The cross-section of the femoral head at 6—6 of FIG. 2 is shown in FIG. 6, which shows aperture 26, the cut-out provided in the femoral head and neck to receive the equivalent cross-section 6A—6A of insert 32. Remaining upstanding cancellous bone is shown, together with remaining cortex, as well as substantially flat and vertical faces 42 provided at the sides, i.e., front and back, and the end of the femoral head by squaring off the same by resecting areas 28. As will be seen from comparing FIGS. 6 and 6A, the cross-section of the head 34 of insert 32 at 6A—6A is adapted to correspond as closely as possible with the cross-section of the aperture 26 provided in the femoral neck and head at 6—6 of FIG. 2.

In FIGS. 2 and 3, the top 36 of insert 32 is shown for purposes of clarity of presentation and understanding, but it is to be understood that head 34 is ordinarily in practice integral with or secured, as by welding or brazing, to femoral cap 46. When said head 34 and cap 46 are not integral, they may, for example, be conventionally secured as by welding surface 36 of head 34 to corresponding interior surface 48 of cap 46. (See FIGS. 8, 9, 10, and 11).

FIGS. 4B, 5B and 6B are the same as FIGS. 4, 5, and 6, but show the inserts of FIGS. 4A, 5A, and 6A in place within the intramedullary canal or femoral shaft and head and cemented therein with medically-acceptable cement 44. Due to the Y-shaped portions 40 of insert 32 at the stem and neck thereof, as shown in FIGS. 4B and 5B, insert 32 is in rigid three-point engagement with the interior of the femoral shaft, so that employment of medically-acceptable cement can be considered optional at the discretion of the performing surgeon.

FIG. 7 is a medial view along line 7—7 of FIG. 2 showing the remodeled femoral head, with the angled top surface elevating from front to back approximately seven degrees from a right-angle line drawn perpendicular to axis 20, cut-out aperture 26 in the femoral head and neck, remaining cortex and cancellous bone, and flat faces 42 provided at the front and back of the femoral head. Although angled 23 degrees, as shown in FIG. 2, and seven degrees from a right-angle line drawn perpendicular to axis 20 as shown in FIG. 7, top surface 42 as shown in FIG. 7 also lies essentially in a plane and presents a flat although angled face.

As shown completely assembled in FIG. 8, with insert 32 in place, head 34 of the insert lies between upstanding portions of cancellous bone and in aperture 26 provided in the femoral head and neck, and is secured within said aperture by medically-acceptable cement. Portions of the cortex also remain, and neck of insert 32 just below the head 34 is seen as resting against the inner surface of the cortex of the medial portion of the femur at approximately the inferior femoral neck or calcar.

As shown, top surface 36 of head portion 34 of insert 32 corresponds essentially to the plane or surface 42 provided by the cut-off 30 on top of the femoral head and is characterized by essentially the same angular disposition, top surface 36 in fact being integral with cap 46 or welded or otherwise secured to internal surface 48 of cap 46.

Figure 9:
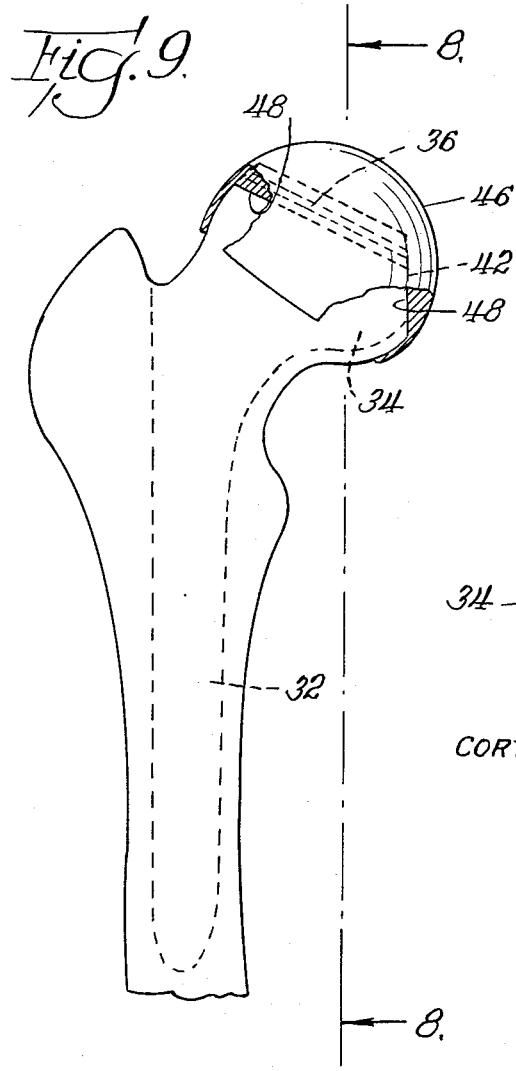
FIG. 9 is a side view partially in section of the upper portion of the femur with insert including the femoral cap in place over the remodeled femoral head.

In FIG. 9 is shown a side view of the femur with the shell or cap 46 in place over the remodeled femoral head, replacement shell or cap 46 itself being either of a unitary nature or prefabricated or fabricated from a generally hemispherical shell and inserts, the flat areas 42 of the remodeled femoral head coinciding with and matching flat faces 48 provided interior of shell or cap 46. At 36 is shown the upwardly-angled top surface of insert 32 at the top or upper surface of head portion 34 thereof, lying between the upper surfaces of the remaining upstanding portions of the remodeled femoral head and neck, all of these aspects as well as the location of the insert stem and neck within the femoral shaft being shown in shadow lines or in partial section. It will again be understood that in practice, head 34 of insert 32 is either integral with cap 46 or secured thereto as by welding surface 36 and cap internal surface 48.

Figure 10:
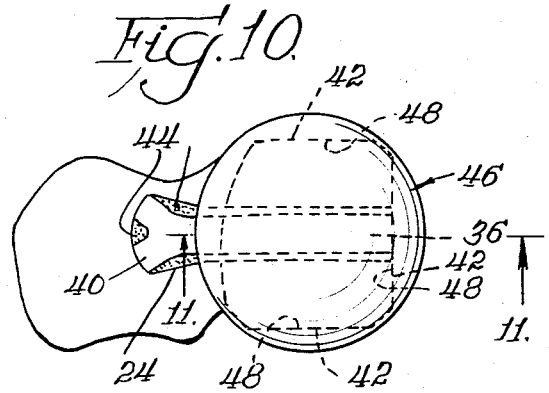
FIG. 10 is a top view (similar to FIG. 1) of the capped femoral head of FIG. 9, showing the greater trochanter, the superior neck, and the remodeled femoral head and lower portion of the insert in shadow lines, before filling of the entry opening.

From FIG. 10 is seen the flat faces 42 of the remodeled femoral head and the mating flat faces 48 interior of cap or shell 46, together with top surface 36 of head 34 of insert 32 (which again is either integral with or secured to corresponding cap internal surface 48). The portion of the opening 24 extending into the superior femoral neck is visible, as well as the Y-shaped portion of the insert 32, as shown being cemented in place within said aperture 24 by means of the optional medically-acceptable cement 44. FIG. 10 is to be compared with FIG. 6B, directly above, as well as with FIGS. 8 and 9, for the best understanding of the relationship of the parts of this assembly. The cap or shell 46 is of course cemented in place over the remodeled femoral head employing medically-acceptable cement, and the opening 24 in FIG. 10 can, if desired, be filled with medically-acceptable cement, bone chips or dust, combinations of the same, or the like, or with a medically-cemented plug, as will be apparent to one skilled in the art. A cross-section of the shell or cap 46 along line 11—11 in FIG. 10 is presented in FIG. 11, and shows the internally-disposed substantially flat surfaces and curves, for close mating engagement with and securement, with medically-acceptable adhesive or cement, to the corresponding contours of the remodeled femoral head. Slanting internal face 48 corresponds to insert head surface 36 and is welded or otherwise secured thereto in cases when insert head 34 and cap 46 are not integral.

FIGS. 12 through 16 require no further discussion or explanation, as all of the various aspects thereof are fully disclosed and explained in the foregoing with reference to the preceding FIGS., especially FIGS. 3 and 7, but also others.

In practice, any convenient and operative order of steps may be employed. Usually, however, an opening is first provided at the superior neck of the femur, as by drilling vertically down the femoral shaft or intramedullary canal, essentially in line with vertical axis 20, as shown in FIG. 2. A specially-shaped reamer or rasp, having the cross-section of openings 24, 24 in FIGS. 4 and 5, as previously indicated, is then preferably employed, and is driven down the femoral shaft and worked up and down therein. Other means of providing the aperture 24 in the femoral shaft may be employed, usually advantageously. A sideblade and guide may also be driven through the superior femoral head and neck, if desired, and these may be employed as guides for performing the remaining osteotomy of the femoral neck and head. Other means may of course be employed with equal facility. In any case, the remaining osteotomy of the femoral neck and femoral head is then completed, usually by sawing, to provide excavation or cut-out 26 in the femoral head, as indicated in FIGS. 2, 7, and 8. A high-pressure water jet is generally employed to remove excess bone and marrow tissue from the intramedullary canal. A plug of innocuous material, such as bone or a medically-acceptable plastic, e.g., polyethylene, may then be placed in the intramedullary canal distal to the expected tip of the stem 38 of insert 32. The appropriate-size femoral insert 32 is then driven down the aperture 24 provided in the intramedullary canal and into the aperture 26 provided in the femoral head and neck. The surgeon can at this point determine whether further stabilization of the insert is required and, if so, employ medically-acceptable cement as shown in FIGS. 4B and 5B for this purpose. In such case, a small tube of cement may be injected or inserted into each of the recesses around the tri-flanged stem and neck of insert 32, as shown in FIGS. 4B and 5B, and additional cement may be inserted or injected around head 34 of insert 32 within the aperture 26 provided in the remaining femoral head, usually employing a flattened inserting instrument and under high pressure. The substantially hemispherical shell or cap 46, integral with or secured to head 34, fits over the remodeled femoral head as shown in FIGS. 8, 9, and 10, and is secured in place thereover by means of medically-acceptable adhesive or cement. The flat faces and other internal contours of cap or shell 46, because of their correspondence and coincidence, lie in close juxtaposition and mating engagement with the corresponding surfaces of the remodeled femoral head and are readily securable thereto to provide an essentially interlocked relationship.

The remodeled and recapped femur, as now provided according to the method of the invention and employing the prosthetic femoral insert according to the invention, is superior in many respects to previously-available femoral replacements. For example, the angles, at which the top surfaces of the remaining upstanding portion of the femoral head and neck are cut, are designed to impart superior load-bearing characteristics to the structure and its operation, inasmuch as these are essentially the angles at which thrust is imparted to the femur or femoral head from the acetabulum or acetabulum prosthesis under conditions of a normal human gait. In addition, the novel means of the invention provides a Y-shaped insert for three-point contact within the intramedullary canal, thereby imparting three-dimensional stability for the insert within the femoral shaft and making employment of medically-acceptable cement unnecessary in many cases or at least leaving it to the option of the attending surgeon whether or not it shall be employed. Further, the retention of a considerable amount of upstanding cancellous bone and cortex above the calcar affords the opportunity for bone growth into the insert in the region of the head of the insert and the femoral head or neck, and particularly within the confines of the surrounding cap and shell. Additionally, the mating engagement of surfaces, especially within the surrounding cap or shell and the remodeled femoral head, again reduces the chance of loosening and increases the chance for permanent adherence of the cap or shell to the remodeled femoral head and of the femoral insert within the intramedullary canal. Other advantages will immediately be apparent to one skilled in the art, for example, the fact that the neck of the femoral insert is seated directly against the inner surface of the cortex of the medial portion of the remodeled femur at the inferior femoral neck or calcar portion thereof.

As previously stated, bony ingrowth into a porous-coated surface or porous surface is highly desirable, for which purpose any acceptable porous coating may be applied to the inner surfaces of the shell or cap or to the surfaces of the femoral insert which are to come into contact with areas of possible future bony ingrowth. At any rate, any or all of the interior surfaces of the cap or shell and any or all of the surfaces of the femoral insert may be coated and preferably are so coated for purposes of facilitating bony ingrowth into the surface thereof.

As far as the material of construction, numerous metals and alloys are known in the art and are available as materials of construction, as well as ceramic and plastic materials, so that the present invention is not to be limited by the materials of construction employed. Any of the materials previously found suitable in the art for similar prosthetic devices may of course be employed, as may any such porous materials or porous-coated materials.

As far as the adhesive or cement employed, this may be any medically-acceptable adhesive or cement, according to the skill and usage of the art, and acrylic bone cement, with or without intermixed bone chips or dust, is particularly suitable, although the invention is in no way to be limited by the type of medically-acceptable adhesive or cement employed, inasmuch as numerous such materials are available and well-known to one skilled in the art.

Further, as far as a porous coating or exterior of the femoral insert of the invention, such may be provided in the form of open-mesh fabrics or gauze or a woven basket type of cover, as is also well established in the art, or in the form of dimpling or surface imperfections, or any equivalent means, and of course the invention is in no way to be limited by whatever means or method may be employed to produce a porous surface on the interior cap or shell of the invention or upon the surface of the femoral insert of the invention, in any such case where a porous surface is provided or desired.

Other advantages of the present invention, which will immediately be apparent to one skilled in the art, are to provide a femoral reconstruction or replacement which minimizes the amount of bone removed from the femoral head and neck; to provide for direct contact of the femoral insert with the inner surface of the medial wall of the femur or calcar; to minimize shear force across the femoral component bone interface by directing the osteotomy of the femoral head and neck at an acute angle, preferably approximately 23 degrees, with respect to a line perpendicular to the vertical axis of the femoral shaft; to provide for a device which is inherently stable and not subject to usual stresses and strains, to decrease the likelihood of loosening, both early and late, in employment of the prosthetic device, as a result of continued use thereof; and finally to allow bony ingrowth into the surface thereof, which is preferably effected by employing a porous surface or a porous-coated surface, while at the same time providing the attending surgeon the option of stabilization with cement until this bony ingrowth occurs.

Some additional comments concerning several of the unique features of the present invention are as follows:

The present osteotomy provides a superior surface which is cut on an acute angle, preferably approximately 23 degrees. This osteotomy thus provides a plane which is perpendicular to the lines of force of the hip during normal gait and therefore decreases the shear force applied to the remodeled femoral head and to the prosthesis and provides for inherent stability thereof. Further, when present, the angling of the superior surface, from front to back at a further acute angle, preferably approximately seven degrees, also provides for these same advantages due to elimination of an additional force and shear factor. As to the femoral cap, usually a metal shell, surrounding the remodeled femoral head, it is likewise inherently stable and minimizes resection of the bone, but allows adequate resection of bone and retention of that which is viable. In addition, its unique combination of interior flat faces and contours, corresponding exactly to those of the remodeled femoral head and providing for close juxtaposition and engagement therewith and securement thereto, provides a type of interclock which is characterized by extreme stability, especially since it is integral with or secured to the head of the femoral insert. As to the neck of the femoral insert, in the finished product it lies in direct contact with the clear and medial femoral cortex, thereby again minimizing the likelihood of any settling during use. Multiple sizes of the femoral insert are of course available so as to accomodate individual differences and permit this advantageous direct contact. So far as is known, the present prosthesis is the first which allows the surgeon an option of cementing or not cementing following introduction of the prosthesis into the intramedullary canal, at least partially due to the Y-shaped cross-section of the insert at its stem and neck, so that the prosthesis may be inserted first and then, if judged appropriate, cement placed along the triflanged stem or neck thereof. In addition, this prosthesis is believed to be the first which combines a metallic shell with a tri-flanged insert having a Y-shaped cross-section, in this case preferably being present at both the stem and the neck thereof. Moreover, the present osteotomy on the femoral head and neck is effected in spaced relation to the calcar, the exact distance being significant only to the extent that substantial upstanding portions of the cancellous bone and cortex above the calcar are retained and angled as previously described according to the principles of the present invention. When a porous material of construction or porous coating is employed, the present prosthesis is the first to combine a shell or cap with a tri-flanged insert and a porous surface, indeed an advantageous combination of elements giving rise to superior use characteristics.

Although the invention has been described for a femoral insert 32 with a head portion 34, which is either integral with cap 46 or which, at its superior surface 36, is secured as by welding or the like to the corresponding interior surface 48 of cap 46, it should be apparent to one skilled in the art that the cap 46 and the lower portion of the insert 32 can be made independent of each other and not secured to each other until after placement and/or securement of the lower portion of the insert within the femoral shaft and within aperture 26 provided in the femoral head, at which time the substantially hemispherical shell or cap 46 can be fitted over the remodeled femoral head, including the upstanding head portion 34 of femoral insert 32, thereby bringing interior surfaces 48 of cap 46 not only into contact with the remaining vertically upstanding portions of the femoral head, but also into contact with superior surface 36 of insert head 34, once again as shown in FIGS. 8, 9, 10. At this point, the cap 46 can be secured in place thereover, and its mating surfaces secured to the corresponding mating surfaces of the femoral head and insert head, by means of medically-acceptable adhesive, cement, or in any other permanent manner.

In such case the superior surface 36 of the insert head 34 is preferably and advantageously angled in the same manner as the upper surface 42 of the remaining vertically-upstanding portions of the femoral head, so as to lie in the same plane therewith, and the corresponding mating surfaces 48 interior of the femoral cap 46 are preferably adapted to lie in the same plane for maximum mating relationship with the surface 36 of the insert head 34 as well as the superior surfaces 42 of the remaining vertically-upstanding portions of the femoral head itself. Thus, the superior surface 36 preferably incorporates the slope from left to right of approximately 23 degrees and the slope from front to back of approximately seven degrees, all as previously described with relation to the superior surface 42 of the remaining vertically-upstanding portions of the femoral head itself.

The interlock between the mating surfaces in the head and cap in such also be improved by provision of rectangular or other preferably non-circular male and female cooperating elements, or tongue and groove elements, or the like, if desired. For purposes of vertical or longitudinal stability of the remodeled joint, however, it will be apparent to one skilled in the art that the preferred form of insert, wherein head 34 and cap 46 are integral, or secured to each other as by welding along mating surfaces 36 and 48, is the preferred structure according to the invention, although the alternative structure may be employed where vertical or longitudinal stability is not considered a paramount factor.

Although the lower portion of the insert and the cap may be formed of different materials of construction, and secured together at the interface between the top surface 36 of insert 34 and the inner surface 48 of cap 26, as indicated in FIG. 8, where both cap and insert are shown as metal, when the cap and insert head are integral they are of course formed of identical material. Moreover, even when they are secured together by welding or the like, they are usually and advantageously formed of identical materials of construction. In fact, a situation in which the lower portion of the insert including head 34 and cap 46 are not formed of the same material of construction is generally not preferred. However, in cases where permanent securement of the opposing surfaces of the unlike materials selected for employment does not present a problem, there is no essential preclusion against the material or construction employed for the cap being different than the material of construction employed for the lower portion of the insert and the head thereof. Usually, both are formed of metal and, ordinarily, of the same metal, which is generally an alloy of some type for maximum strength and minimum weight.

In conclusion, from the foregoing, it is apparent that the present invention provides a novel femoral head replacement and reconstruction technique, involving minimum bone removal, as well as a novel femoral insert for use therein, all having the foregoing enumerated characteristics and advantages.

It is to be understood that the invention is not to be limited to the exact details of construction, operation, or to the exact materials of construction, compositions, methods, procedures, or embodiments shown and described, as obvious modifications and equivalents will be apparent to one skilled in the art, and the invention is therefore to be limited only by the full scope of the appended claims.

I claim:

1. A femoral insert, adapted to be secured in a femoral shank as a part of a femoral hip joint replacement, comprising an elongated shaft with a longitudinal axis generally corresponding to the vertical axis of a femoral shank, said insert comprising a stem portion, a neck portion, and a head portion constituting an offset to the longitudinal axis of said shaft, said stem, neck, and head portions being both solid and integral, said head portion having a cross-section when viewed from its top of the nature of an elongated rectangle, to permit seating thereof between two vertically-upstanding portions of a remodeled femoral head having an opening therebetween generally corresponding to the cross-section of said head portion, and including a femoral cap on said head portion, wherein said shaft is flanged along at least a lower portion thereof and wherein a groove is formed on a posterior surface of said shaft along its longitudinal axis, so as to permit three-point contact of said shaft with the interior cortex of said femoral shank when said flanged portion is in place therein.

2. The insert of claim 1, wherein said neck portion of said insert is adapted to be seated on cortex at the calcar of said femur and is curvedly contoured to correspond approximately to the interior contour of the calcar of said femur.

3. The insert of claim 1, wherein the head portion of said insert has an essentially downwardly vertical face at the end thereof.

4. The insert of claim 3, wherein the front, back, and end surfaces of said head of said insert are substantially flat vertical planes.

5. The insert of claim 1, wherein said shaft of said insert comprises a Y-shaped cross-section along at least a portion thereof.

6. The insert of claim 5, wherein said Y-shaped cross-section is present at said stem portion and said neck portion of said insert.

7. The insert of claim 1, having a porous surface.

8. A femoral insert, adapted to be secured in a femoral shank as a part of a femoral hip joint replacement, comprising an elongated shaft with a longitudinal axis generally corresponding to the vertical axis of a femoral shank, said insert comprising a stem portion, a neck portion, and a head portion constituting an offset to the longitudinal axis of said shaft, said stem, neck, and head portions being integral, said head portion having a cross-section when viewed from its top of the nature of an elongated rectangle, to permit seating thereof between two vertically-upstanding portions of a remodeled femoral head having an opening therebetween generally corresponding to the cross-section of said head portion, said femoral insert further including a femoral cap, said femoral cap comprises an outer hemispherical shell substantially corresponding to the normal femoral head and of a size approximately that of the femoral head being replaced, and has an inner surface and contours adapted to correspond to the superior surface of a remodeled femoral head which is essentially squared off at its front, back, and end, and which has a downwardly-slanting superior surface resected therein, which downwardly-slanting surface is at an acute angle with respect to a line normal to the vertical axis of the femoral shaft to which said remodeled femoral head is attached, the interior of said cap having surfaces therein which correspond to the outer surfaces of said remodeled femoral head for positive mating relation of said surfaces when said cap is in place over said remodeled femoral head.

9. The insert of claim 8, wherein said cap has a porous interior surface.

10. The insert of claim 8, wherein said downwardly-slanting superior surface angles downwardly at a first acute angle and is also angled upwardly from front to back at a second acute angle.

11. The insert of claim 8, wherein said acute angle is between about twenty and thirty degrees.

12. The insert of claim 11, wherein said angle is about 23 degrees.

13. The insert of claim 10, wherein said second acute angle is less than about ten degrees.

14. The insert of claim 13, wherein said second acute angle is about seven degrees.

15. A method of providing a femoral hip joint replacement comprising the steps of providing an opening at the superior neck of the femur, providing an elongated excavation within the femoral shank generally corresponding to the shaft of a femoral inset to be inserted therein and essentially in line with the vertical axis of said femoral shank, providing an elongated aperture in said femoral head so as to leave two upstanding vertical sections of said femoral head with a generally elongated rectangular aperture therebetween, imparting a superior surface to the remaining vertically-upstanding portions of said femoral head which slants downwardly at an acute angle with respect to a line normal to the vertical axis of said femoral shaft to present a plane which is adapted to be essentially perpendicular to the lines of force imparted to the femoral portion of a hip joint during normal human gait, providing a femoral insert within the excavated portion of said femoral shaft, said insert comprising an elongated shaft having a longitudinal axis generally corresponding to the vertical axis of said femoral shank and having a stem portion, a neck portion, and an offset head portion, said head portion being of generally elongated rectangular cross-section and adapted to lie within the generally elongated rectangular aperture provided in said femoral head between said remaining vertically-upstanding portions of said remodeled femoral head providing, said head portion of said insert with a femoral cap, and securing said shaft within said femoral shaft, said head portion in place between said remaining vertically-upstanding portions of said remodeled femoral head, and said femoral cap in place over said remodeled femoral head.

16. The method of claim 15, wherein said superior surface of said remaining vertically-upstanding portions of said femoral head angle downwardly between about twenty and thirty degrees with respect to said normal line.

17. The method of claim 16, wherein said superior surface of said remaining vertically-upstanding portions of said femoral head is angled downwardly about 23 degrees with respect to said normal line.

18. The method of claim 15, wherein the said superior surface is angled downwardly at a first acute angle and is also angled upwardly from the front to the block of said superior surface at a second acute angle.

19. The method of claim 16, wherein the said superior surface is also angled upwardly from the front to the back of said superior surface at an angle less than about ten degrees.

20. The method of claim 7, wherein the said superior surface is also angled upwardly from the front to the back of said superior surface at an angle of about seven degrees.

21. The method of claim 15, including the step of providing said shaft of said insert with a flange along at least a lower portion thereof, when viewed along its longitudinal axis, so as to provide three-point contact of said flanged portion of said shaft within said femoral shank.

22. The method of claim 21, including the step of providing said shaft of said insert with a Y-shaped cross-section along at least a portion thereof.

23. The method of claim 22, including the step of providing said Y-shaped cross-section at said stem portion and said neck portion of said insert.

24. The method of claim 15, wherein the shaft of said insert is secured within the femoral shank without the employment of medically-acceptable cement.

25. The method of claim 15, wherein the shaft of said femoral insert is secured within the femoral shank with the aid of medically-acceptable cement.

26. The method of claim 15, wherein the head portion of said insert is secured within said aperture with the aid of medically-acceptable cement.

27. The method of claim 15, including the step of providing the head of said insert with an essentially downwardly-vertical face at the end of said offset.

28. The method of claim 15, wherein the neck of said insert is seated on the inner surface of the cortex of the remodeled femur at the calcar or femoral neck.

29. The method of claim 15, including the step of providing the femoral insert with a curved contour at its neck to correspond substantially with the contour of the inner surface of the cortex of the calcar or inferior femoral neck and wherein the insert is seated against the inner surface of the cortex of the remodeled femur at the calcar.

30. The method of claim 16, wherein the end of said femoral head is squared off at the end of said slanting superior surface thereof.

31. The method of claim 29, wherein the front, back, and end of said femoral head are squared off.

32. The method of claim 31, wherein the squaring off of said femoral head presents substantially flat and vertical faces on the front, back, and end of said remodeled femoral head for close and mating engagement with corresponding surfaces provided interior of said femoral cap which is secured in place over said femoral head.

33. The method of claim 15, including the step of providing said femoral cap in a substantially hemispherical shape having an outer size and contour essentially corresponding to the outer surface and contour of the femoral head being replaced.

34. The method of claim 33, wherein internal faces and contours of said cap correspond to surfaces provided in said remodeled femoral head and lie in close juxtaposition and in mating engagement with the corresponding surfaces of said remodeled femoral head when said cap is in place thereover.

35. The method of claim 34, wherein said cap is secured over the end of said remodeled femoral head with the aid of medically-acceptable cement.

36. The method of claim 15, including the step of providing said insert with a porous surface.

37. The method of claim 34, including the step of providing said shaft with a porous surface and said cap with a porous interior surface.

38. The method of claim 15, wherein, after completion of the remodeling of the femoral head, the opening originally provided in the superior neck of the femur is closed.

39. A femoral insert, adapted to be secured in a femoral shank as a part of a femoral hip joint replacement, comprising an elongated shaft with a longitudinal axis generally corresponding to the vertical axis of a femoral shank, said insert comprising a stem portion, a neck portion, and a head portion constituting an offset to the longitudinal axis of said shaft, said stem, neck, and head portions being both solid and integral, said head portion having a cross-section when viewed from its top of the nature of an elongated rectangle, to permit seating thereof between two vertically-upstanding portions of a remodeled femoral head having an opening therebetween generally corresponding to the cross-section of said head portion, wherein said shaft is flanged along at least a lower portion thereof, and wherein a groove is formed on a posterior surface of said shaft along its longitudinal axis, so as to permit three-point contact of said shaft with the interior cortex of said femoral shank when said flanged portion is in place therein.

40. The insert of claim 39, wherein said head portion comprises a superior surface which angles downwardly between about twenty and about thirty degrees with respect to a line drawn normal to the longitudinal axis of said shaft.

41. The insert of claim 40, wherein said downward angle is about 23 degrees with respect to said normal line.

42. A femoral insert, adapted to be secured in a femoral shank as a part of a femoral hip joint replacement, comprising an elongated shaft with a longitudinal axis generally corresponding to the vertical axis of a femoral shank, said insert comprising a stem portion, a neck portion, and a head portion constituting an offset to the longitudinal axis of said shaft, said stem, neck, and head portions being integral, said head portion having a cross-section when viewed from its top of the nature of an elongated rectangle, to permit seating thereof between two vertically-upstanding portions of a remodeled femoral head having an opening therebetween generally corresponding to the cross-section of said head portion, wherein said head portion comprises a superior surface which angles downwardly about twenty and about thirty degrees with respect to a line drawn normal to the longitudinal axis of said shaft, wherein said superior surface angles downwardly at said acute angle and is also angled upwardly from the front to the back of said superior surface at a second acute angle.

43. The insert of claim 42, wherein the said superior surface is angled from the front to the back of said superior surface at a second acute angle less than about ten degrees.

44. The insert of claim 43, wherein said second acute angle is about seven degrees.

* * * * *

UNITED STATES PATENT AND TRADEMARK OFFICE
CERTIFICATE OF CORRECTION

PATENT NO. : 4,532,661  Page 1 of 2

DATED : August 6, 1985

INVENTOR(S) : Alan A. Halpern

It is certified that error appears in the above-identified patent and that said Letters Patent is hereby corrected as shown below:

Title page, [76] Inventor:; "2830 Duke St. " should read -- 1400 Low Road --
Title page, [56] References Cited, FOREIGN PATENT DOCUMENTS, second column; "8/1975" should read -- 5/1973 --
Col. 1, line 35; "inury " should read -- injury --
Col. 2, line 48; "may employed" should read -- may be employed --
Col. 5, line 2; "to" should read -- or --
Col. 6, line 36; "verticle" should read -- vertical --
Col. 10, line 46; after "usually" insert -- less --
Col. 11, line 63; "facilitaing" should read -- facilitating --
Col. 12, line 68; "interclock" should read -- interlock --
Col. 13, line 4; "clear" should read -- calcar --
Col. 13, line 7; "accomodate" should read -- accommodate --
Col. 13, line 50; "9, 10." should read -- 9, and 10. --
Col. 14, line 6; after "such" insert -- case can --
Col. 15, line 39; after "of" insert -- said head portion and including a femoral cap on"

Col. 15, lines 40 & 41; delete "said femoral insert further including a femoral cap,"
Col. 15, line 41; before "said" insert -- wherein --
Col. 16, line 7; "inset" should read -- insert --

UNITED STATES PATENT AND TRADEMARK OFFICE
CERTIFICATE OF CORRECTION

PATENT NO. : 4,532,661

DATED : August 6, 1985

INVENTOR(S) : Alan A. Halpern

It is certified that error appears in the above-identified patent and that said Letters Patent is hereby corrected as shown below:

Col. 16, line 29; "head providing," should read -- head, providing --

Col. 16, line 38; "head angle" should read -- head is angled --
Col. 16, line 47; "block" should read -- back --
  line 3)
Col. 16, line 53; "claim 7" should read -- claim 17 --
Col. 17, line 56; delete the comma "," after "15"
Col. 18, line 44; before "about" insert -- between --

Signed and Sealed this

Third Day of December 1985

[SEAL]

Attest:

DONALD J. QUIGG

Attesting Officer

Commissioner of Patents and Trademarks